(12) United States Patent
Hsu

(10) Patent No.: US 9,816,125 B2
(45) Date of Patent: Nov. 14, 2017

(54) TEST STRIP, DETECTING DEVICE AND DETECTING METHOD

(71) Applicant: YSP Co., Ltd, Hsinchu (TW)

(72) Inventor: Tien-Tsai Hsu, Xinpu Township, Hsinchu County (TW)

(73) Assignee: YSP CO., LTD., Hsinchu (TW)

( * ) Notice: Subject to any disclaimer, the term of this patent is extended or adjusted under 35 U.S.C. 154(b) by 544 days.

(21) Appl. No.: 14/170,787

(22) Filed: Feb. 3, 2014

(65) Prior Publication Data

US 2014/0224672 A1    Aug. 14, 2014

(30) Foreign Application Priority Data

Feb. 8, 2013  (TW) .............................. 102105441 A

(51) Int. Cl.
*C12Q 1/00*    (2006.01)
*G01N 27/327*  (2006.01)

(52) U.S. Cl.
CPC ......... *C12Q 1/001* (2013.01); *G01N 27/3272* (2013.01); *G01N 27/3274* (2013.01)

(58) Field of Classification Search
CPC ............. G01N 27/3272; G01N 27/327; G01N 33/48707; G01N 27/48; G01N 27/26; G01N 27/3274; G01N 33/49; G01N 33/80; G01N 33/26; C12C 1/00; C12C 1/02; C12C 1/006; C12C 1/34; C12C 1/54
See application file for complete search history.

(56) References Cited

U.S. PATENT DOCUMENTS

| 6,841,052 | B2* | 1/2005 | Musho ............... G01N 27/3274 204/401 |
| 7,258,769 | B2 | 8/2007 | Cui et al. |
| 8,080,153 | B2 | 12/2011 | Feldman et al. |
| 2007/0251836 | A1 | 11/2007 | Hsu |
| 2010/0270177 | A1* | 10/2010 | Fujiwara ............... C12Q 1/001 205/777.5 |
| 2011/0053289 | A1* | 3/2011 | Lowe ................... B01L 3/5027 436/501 |
| 2011/0139634 | A1 | 6/2011 | Chou et al. |
| 2011/0297557 | A1* | 12/2011 | Wu ..................... G01N 27/3274 205/792 |
| 2014/0262833 | A1* | 9/2014 | Musho ............... G01N 27/3272 205/782 |

FOREIGN PATENT DOCUMENTS

| CN | 101271106 A | 9/2008 |
| CN | 101173884 B | 7/2010 |
| CN | 102128932 A | 7/2011 |
| EP | 0 537 761 A2 | 4/1993 |
| WO | WO 2004/113910 A1 | 12/2004 |
| WO | WO 2005/045414 A1 | 5/2005 |

* cited by examiner

*Primary Examiner* — Gurpreet Kaur
(74) *Attorney, Agent, or Firm* — Muncy, Geissler, Olds & Lowe, P.C.

(57) ABSTRACT

A test strip, a detecting device, and a detecting method are disclosed. The test strip includes a first specimen path, a first electrode set, a second specimen path, a second electrode set, and a reaction reagent. When the specimen contacts the first electrode set and the second electrode set, a first pulse signal and a second pulse signal are generated for obtaining a flow time of the specimen. When the specimen contacts the reaction reagent, the analyte concentration of the specimen can be obtained, and the concentration of the analyte can be corrected by the flow time.

25 Claims, 16 Drawing Sheets

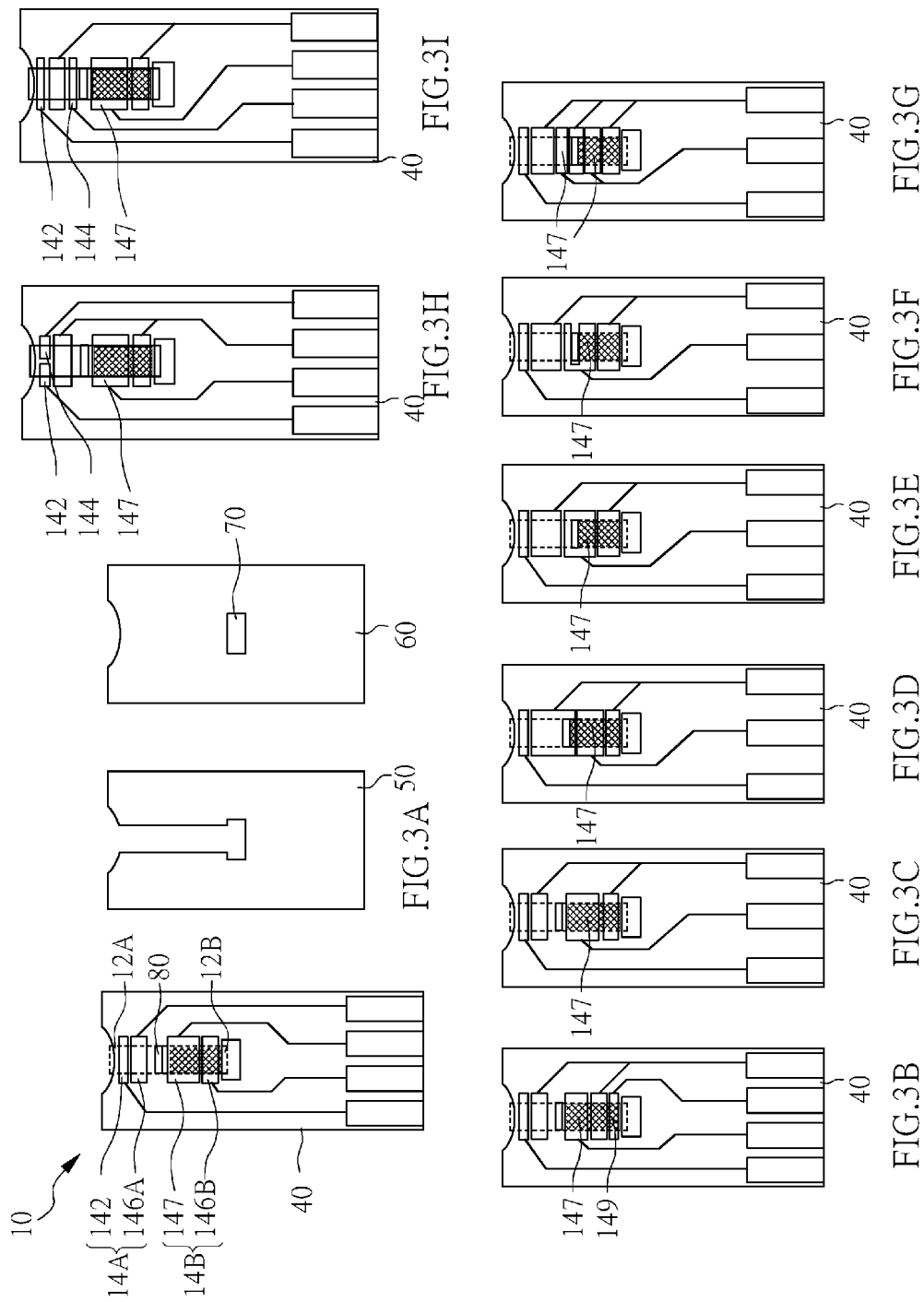

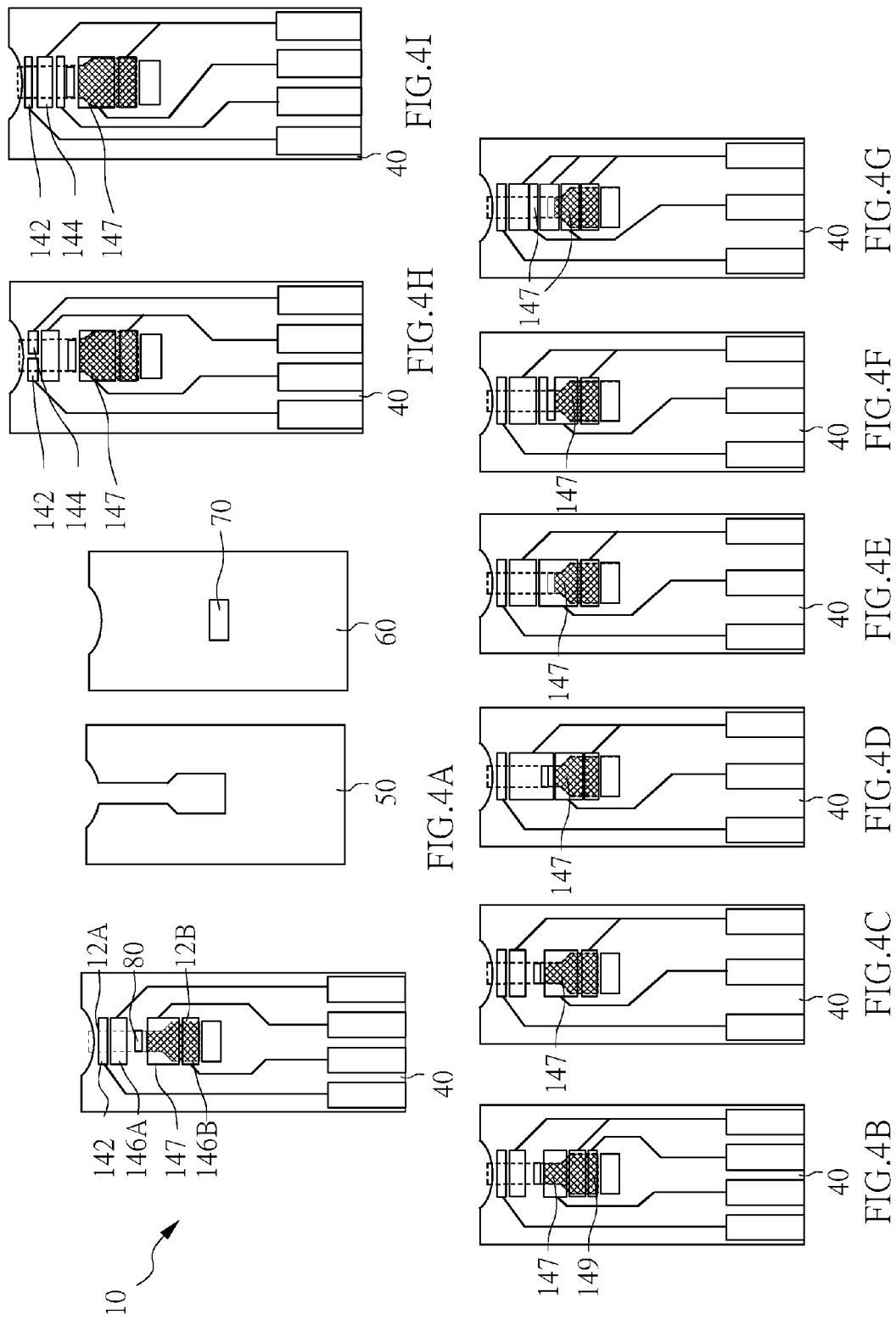

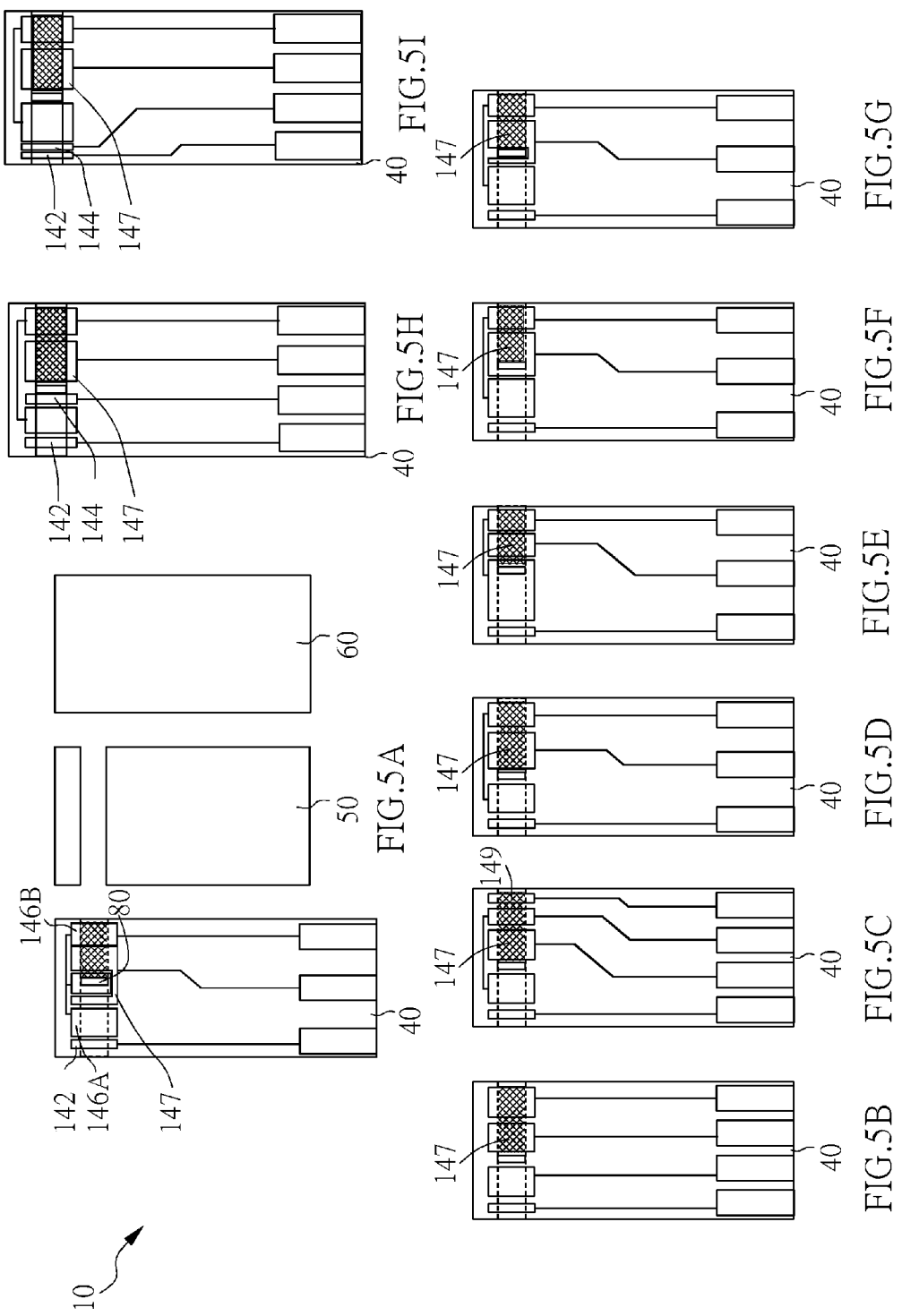

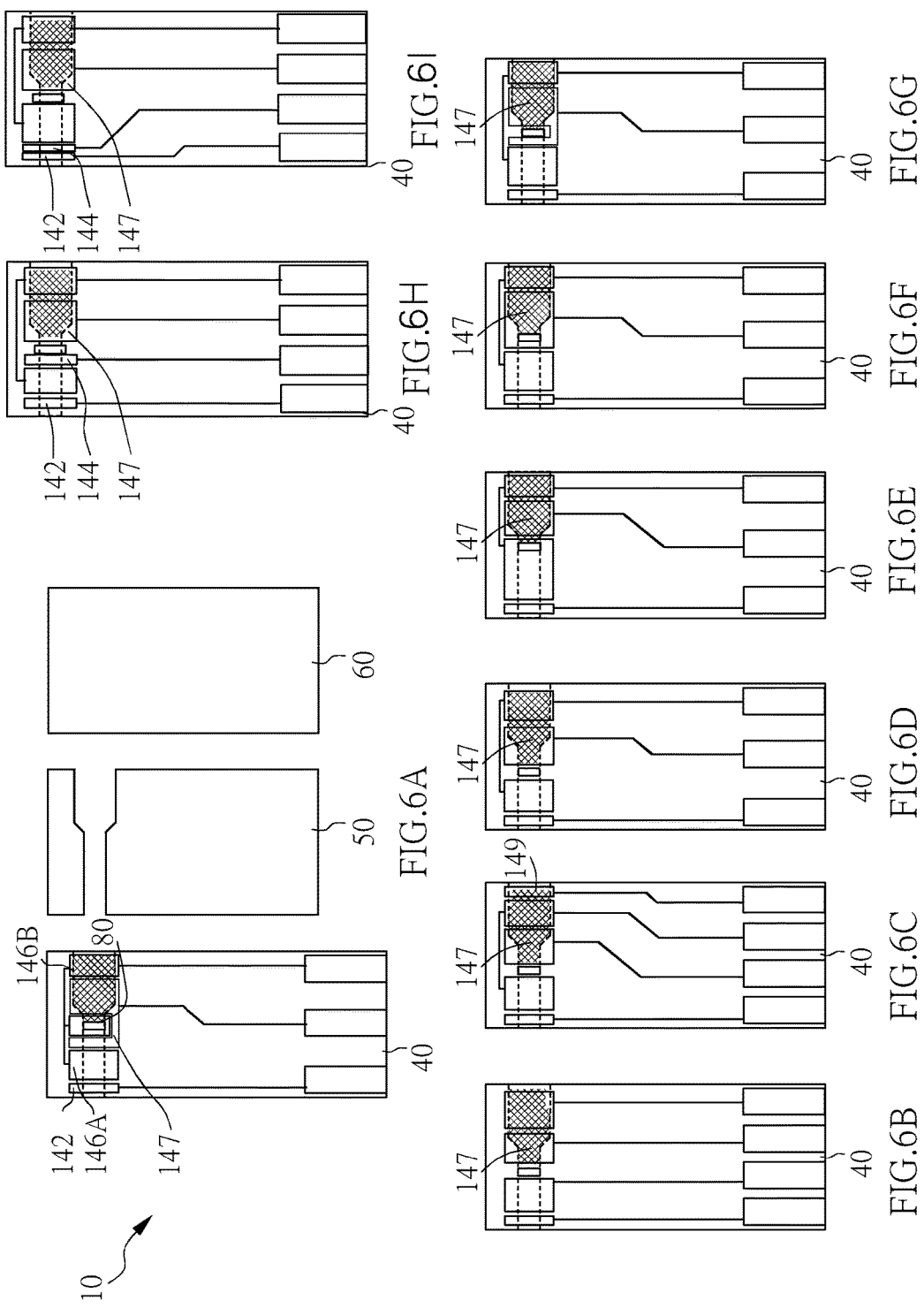

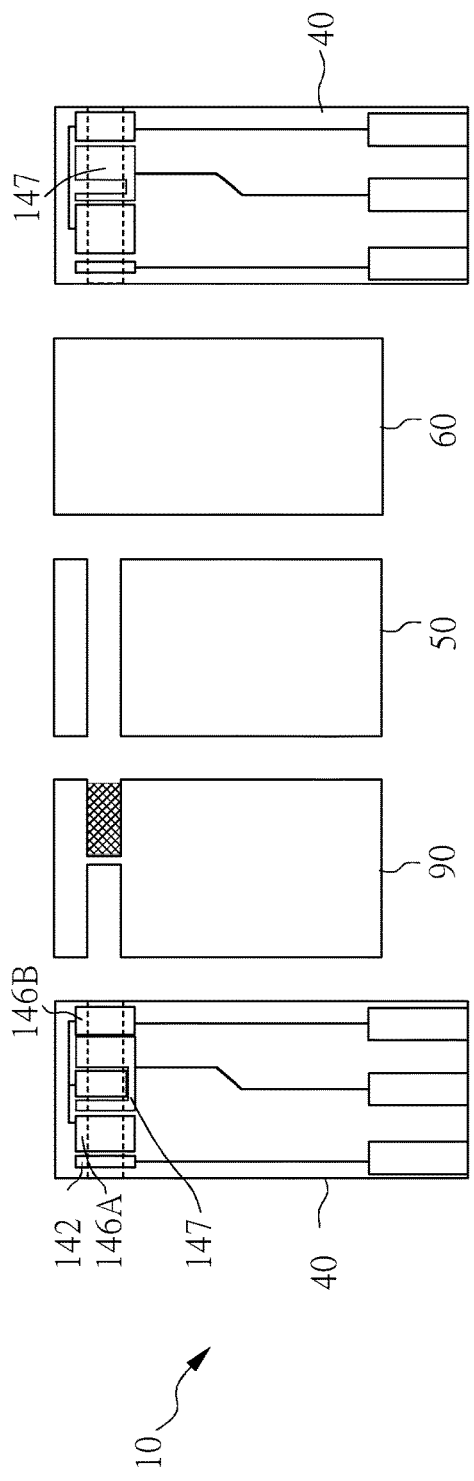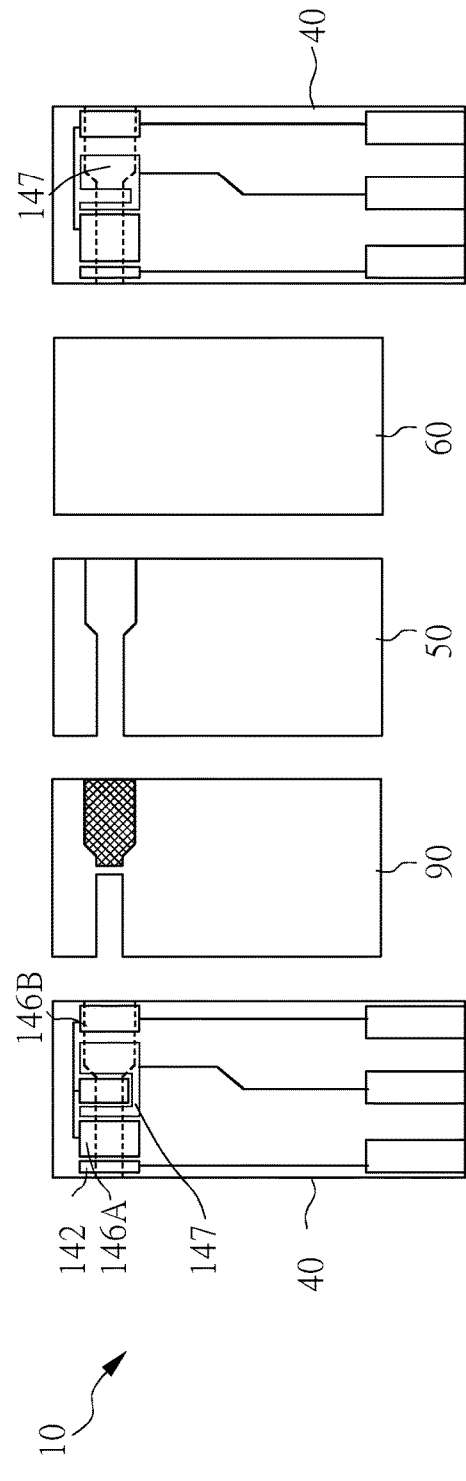

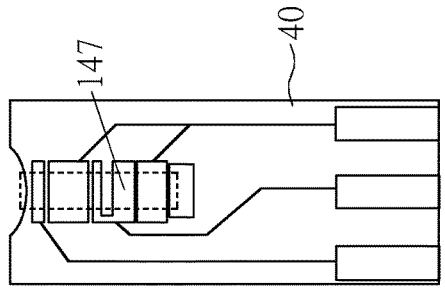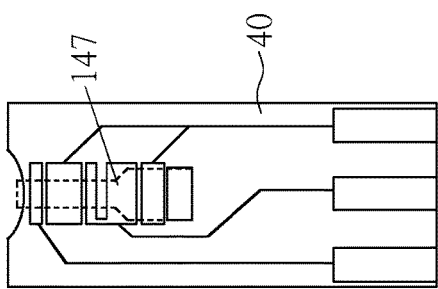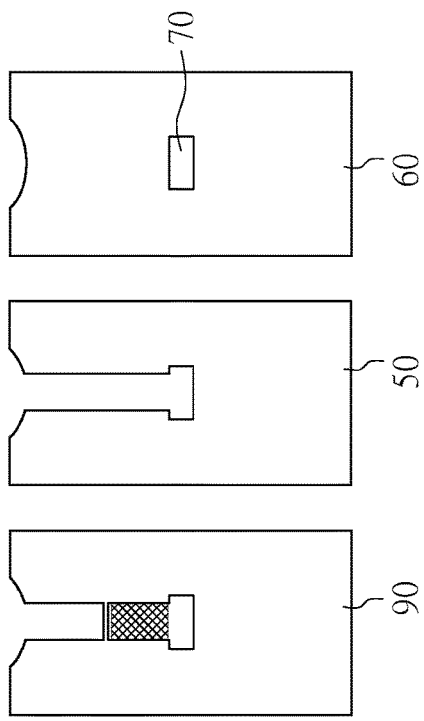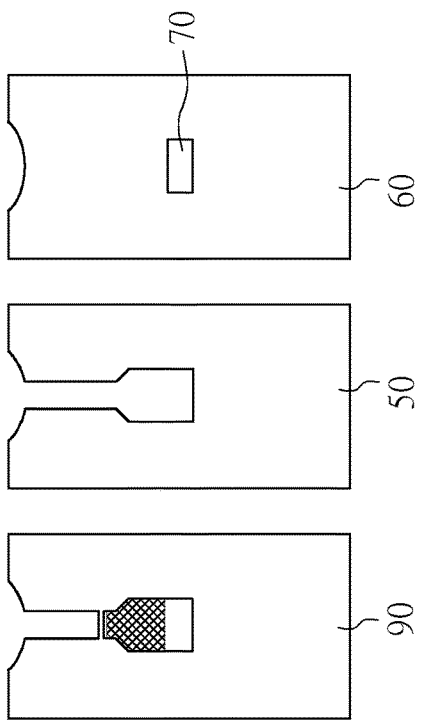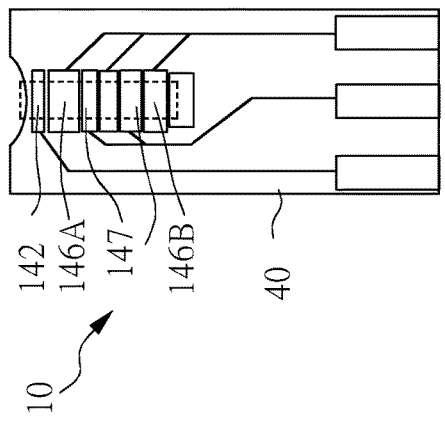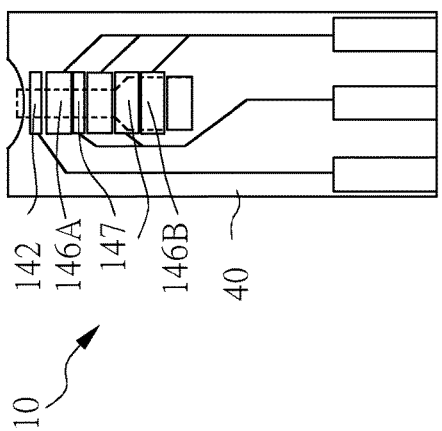

TEST STRIP, DETECTING DEVICE AND DETECTING METHOD

BACKGROUND OF THE INVENTION

1. Field of the Invention

The present invention relates to a test strip, a detecting device, and a detecting method, and more particularly, to a test strip, a detecting device, and a detecting method used to obtain a flow time of a specimen and use the flow time to correct a concentration of the analyte of the specimen.

2. Description of the Related Art

Electrochemical bio-sensors have been widely adopted to find out the concentration of the analyte in a liquid specimen, such as blood or urine. There are many kinds of electrochemical bio-sensors, such as blood glucose sensors, cholesterol sensors, uric acid biosensors, and lactic acid biosensors. In particular, blood glucose sensors have become indispensable for diabetics. Generally, a blood glucose sensor is formed in a strip shape and comprises at least two electrodes such as a working electrode and a reference electrode for receiving electrical signals proportional to the concentration of the blood glucose in a blood sample and transmitting the electrical signals to a blood glucose meter to indicate the blood glucose level.

On the other hand, whole blood viscosity test can provide reliable reference to the diagnosis and treatment of pre- or post-thrombus in many research and clinical experiments. Numerous diseases such as hypertension, cardiopathy, coronary artery heart disease (CAHD), myocardial infarction, diabetic, malignant tumor and chronic hepatitis are highly related to blood viscosity. Blood viscosity could be affected by the size, shape and hematocrit of red blood cells, which are the major part of the blood; although white blood cells and hematoblasts also could affect the blood viscosity; therefore, hematocrit (HCT) is the key factor in deciding the blood viscosity. Furthermore, when the blood viscosity increases, there will be more resistance in the blood, making it difficult to supply blood to the heart, brain, liver and kidney. As less blood is supplied, the symptoms could become worse; therefore, the blood viscosity has become an important index in monitoring the disease.

In order to measure the blood viscosity, there are many types of viscometer, such as capillary viscometer, cone and plate viscometer, coaxial cylinder viscometer, and pressure sensing viscometer, in which capillary viscometer is the most popular type. In a capillary viscometer, when parameters such volume, pressure difference, capillary diameter, and capillary length are constant, then the viscosity of the fluid is proportional to the time required to flow through the capillary; therefore, when the fluid is filled in the capillary, the viscosity of the fluid is obtained by using Poiseuiller's principle. However, there are some restrictions in using the capillary viscometer, for example, the capillary have to be straight, long and round in its cross section, the length to diameter ratio of the capillary usually needs to be more than 200, and the diameter of the capillary is larger or equal to 1 mm, and so on. Besides, the capillary viscometer has large equipment size, it needs a lot of sample volume to process and tends to require long reaction time; therefore, it is not easy to clean the capillary viscometers, and it is not convenient to carry the capillary viscometer with the patient to detect the blood viscosity in real time. When it is necessary to obtain blood viscosity data from a group of people, it takes a great amount of time in detecting blood viscosity from each one of them and it requires getting enough specimens from them; therefore, it is inefficient and also not cost-effective.

Apart from the method for measuring blood viscosity as depicted above, US patent application US2007/0251836A1 disclosed an electrochemical sensor and method for analyzing a liquid sample, in which the electrochemical sensor comprises a channel for delivering the liquid sample; and a first conducting portion and a second conducting portion separated and exposed in the channel; wherein the first conducting portion generates a first pulse signal when it is contacted by the liquid sample, and the second conducting portion generates a second pulse signal when it is contacted by the liquid sample. The electrochemical sensor obtains viscosity of the liquid sample according to a time difference between the first and second pulse signals. Generally an electrochemical sensor provides a voltage no higher than 0.5V to save power and to avoid triggering unnecessary reactions; however, the signal could be very weak and unstable between the liquid sample such as blood and the electrodes, it could be covered by background noises and is difficult to be detected. Furthermore, the electrochemical sensor can be used to correct the concentration of blood glucose, to do so, the electrochemical sensor has to include an enzyme in its channel. In order to save space for test strip, the electrode set for detecting the blood glucose concentration is disposed between the first conducting portion and the second conducting portion, when the liquid sample flows into the channel, the electrode set begins detection at the same time. In other words, the reaction of the enzyme and the detection of the flow time happen in the same channel and could easily interfere with each other; besides, the enzyme disposed on the electrode set also comprises mixtures such as polymeric binders, stabilizers, buffers, surfactants, which could cause the fluidity of the liquid sample to change and often lead to differences in flow time detection. Besides, since the enzyme is provided for reacting with the analyte of the liquid sample to detect the flow time, the flow time signal will not be obtained until the blood samples reacted with the enzyme, otherwise a weak signal or a delayed signal will be detected. Therefore, the prior art technique cannot provide stable detection results and often fails to reproduce itself.

U.S. Pat. No. 7,258,769 uses enzymes to react with blood samples to detect the fluidity of blood and the concentration of blood glucose, when enzymes are added to the test strip, the following reactions would occur:

Glucose+Gox-FAD→Gluconic acid+Gox-FADH$_2$

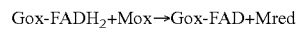

Gox-FADH$_2$+Mox→Gox-FAD+Mred

In the reaction formula, Gox stands for Glucose Oxidase, which reacts with blood glucose to transform into a reduced state, and then the reduced Gox reacts with electron transfer mediators to let the electron transfer mediators transform into a reduced state. Afterwards, the reduced electron transfer mediators would spread to the surface of the electrode and are oxidized by the anode, thereby generating a current for obtaining the concentration of blood glucose. When performing the fluidity detection, it is necessary to wait for blood glucose to react with enzymes to generate a detectable signal, however, by that time the blood may has already flowed through the electrode, so the generated signal does not reflect the real fluidity. Therefore, enzymes disposed in the channel can be used for detecting blood glucose but not for determining the flow time. Since the detection signal can only be generated after the blood sample reacts with enzymes, there will be a time difference between the actual fluidity and the measured fluidity.

U.S. Pat. No. 8,080,153 proposed a method and a system of determining a hematocrit-corrected concentration value of an analyte in a sample. The method comprising: using three reference electrodes with a working electrode in a sampling area to determine a fill time of the sample on the test strip, using enzymes in the sampling area to detect a concentration of the analyte, and then calculating a hematocrit-corrected concentration of the analyte using an empirical formula with the fill time. FIGS. 1A and 1B show FIGS. 4 and 5 of the patent, respectively. As shown in FIG. 1A of this patent, it is clear that when the hematocrit increases, the fill time values tend to scatter, which implies that the patent does not do well in reproducing itself. As show in FIG. 1B, when the hematocrit increases, the concentration of blood glucose reduces, and the number of red blood cells increases. Red blood cells tend to affect the reaction between electron transfer mediators and blood glucose; besides, blood plasma could affect the diffusion of electron transfer mediators as well, so the concentration of blood glucose could be lower than expected. In FIG. 1A, when the fill time is 0.8, it is difficult to determine the hematocrit (which could be 55% or 65%), which in turn would affect the value used to compensate the blood glucose; in other words, this patent could obtain an undesired corrected concentration of the analyte. Generally a male adult has a hematocrit value of between 39 to 50%, while a female adult could has a hematocrit value of between 36 to 45%. A diabetic often suffers from other complications such as high blood pressure, anemia or other heart disease, so the hematocrit of the diabetic could easily become abnormal. When the hematocrit exceeds the normal range, the concentration of the blood glucose could have apparent deviations and needs to be corrected to avoid erroneous judgement and even putting life in danger.

Since the prior art techniques cannot precisely obtain blood viscosity within a short amount of measurement time. The present invention discloses a test strip, a detecting device, and a detecting method to solve the problems present in the prior art techniques.

SUMMARY OF THE INVENTION

It is an object of the present invention to provide a test strip and a detecting device to detect a specimen for not only detecting the flow time and the concentration of the analyte of the specimen, but also correcting the concentration of the analyte by using the flow time to accurately detect the concentration of the analyte. In order to avoid affecting the flow characters of the specimen itself, it increases the capture of signals by enhancing the voltage, and sets the working electrode as the electrode that used to detect the flow time at the same time; therefore, the sample path can reduce exposure to reaction reagents to enhance the accuracy of the flow time. In order to achieve the above object, the present invention provides a test device comprising: a test strip and an electrochemical instrument. The test strip includes a first specimen path, a first electrode set, a second specimen path, a second electrode set and a reaction reagent, wherein the first sample path is connected in series with the second sample path. The first specimen path includes an inlet end; the first electrode set has at least a portion thereof disposed in the first specimen path, and the first electrode set at least includes a first electrode and a first reference electrode. The second specimen path includes a discharge end; the second electrode set is disposed in the second specimen path, and the second electrode set has at least a working electrode and a second reference electrode. Wherein, a first impulse signal is generated when the specimen is in contact with the first electrode and the first reference electrode, and a second impulse signal is generated when the specimen is in contact with the first reference electrode and the working electrode, thereby obtaining a flow time of the specimen according to the first impulse signal and the second impulse signal. The reaction reagent is disposed in the second specimen path, and the reaction reagent at least includes an enzyme for detecting a concentration of the analyte of the specimen. The electrochemical instrument is electrically connected to the test strip for obtaining the flow time and the concentration of the analyte, and then the flow time can be used to correct the concentration of the analyte.

It is another object of the present invention to provide a detecting method for detecting a specimen; the detecting method is used to detect the flow time of the specimen and a concentration of the analyte, and to correct the concentration of the analyte by the flow time to accurately detect the concentration of the analyte. In order to avoid affecting the flow characters of the specimen itself, it increases the capture of signals by enhancing the voltage, and sets the working electrode as the electrode that used to detect the flow time at the same time; therefore, the sample path can reduce exposure to reaction reagents to enhance the accuracy of the flow time. In order to achieve the above object, the present invention provides a detecting method using an electrochemical instrument to detect a specimen, the detecting method comprising the following steps: providing the test strip; providing a first voltage to the first electrode, and providing a second voltage to the working electrode; receiving the specimen in the first specimen path and the second specimen path; recording a first impulse signal generated when the specimen is in contact with the first electrode and the first reference electrode, and recording a second impulse signal generated when the specimen is in contact with the first reference electrode and the working electrode; using the first impulse signal and the second impulse signal to obtain a flow time of the specimen; providing a reaction voltage to the working electrode; enabling an electrochemical reaction between the reaction reagent and the analyte of the specimen; using the electrochemical reaction to calculate an uncorrected concentration of the analyte; and using the flow time to correct the uncorrected concentration of the analyte.

BRIEF DESCRIPTION OF THE DRAWINGS

FIG. 2 to FIG. 12B illustrate various structures of the test strip according to an embodiment of the present invention.

DETAILED DESCRIPTION OF THE PREFERRED EMBODIMENT

The advantages and innovative features of the invention will become more apparent from the following detailed description when taken in conjunction with the accompanying drawings.

The present invention provides a detecting device for detecting a specimen, wherein the detecting device detects the flow time of the specimen and the concentration of the analyte for using the flow time to correct the concentration of the analyte. In an embodiment of the present invention, the detecting device can be used as a blood glucose detecting device.

Figure 1A:
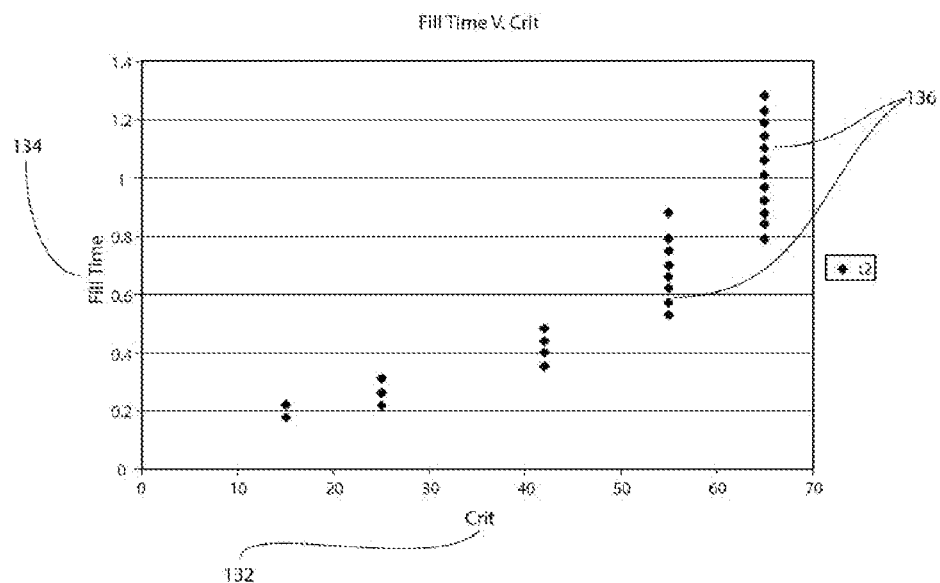
FIG. 1A illustrates a relation between hematocrit and fill times.
Figure 1B:
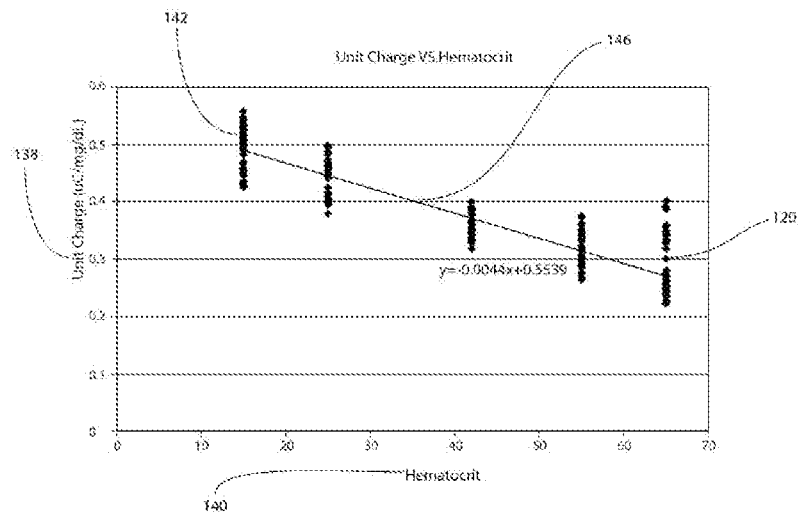
FIG. 1B illustrates a relation between hematocrit and reaction signals of the analyte.
Figure 2:
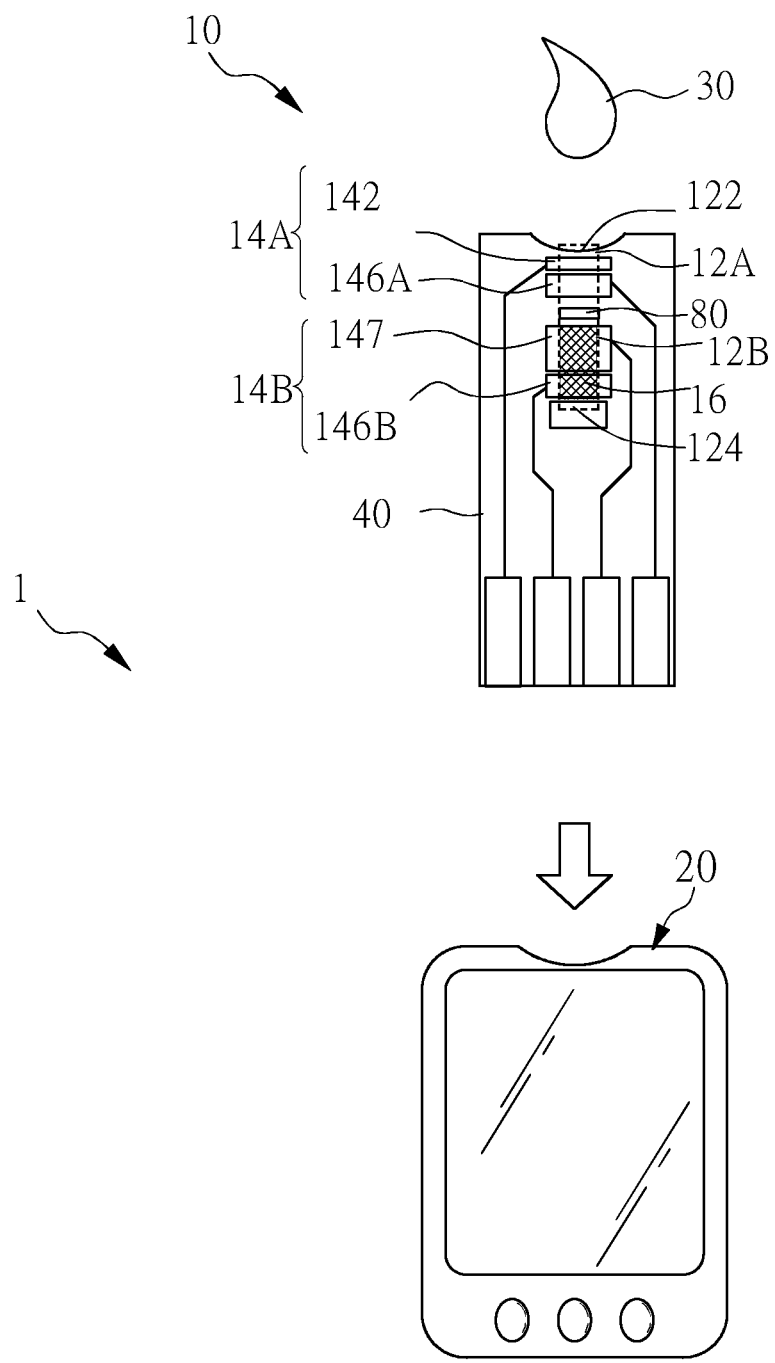
Figures 9A, 9B:
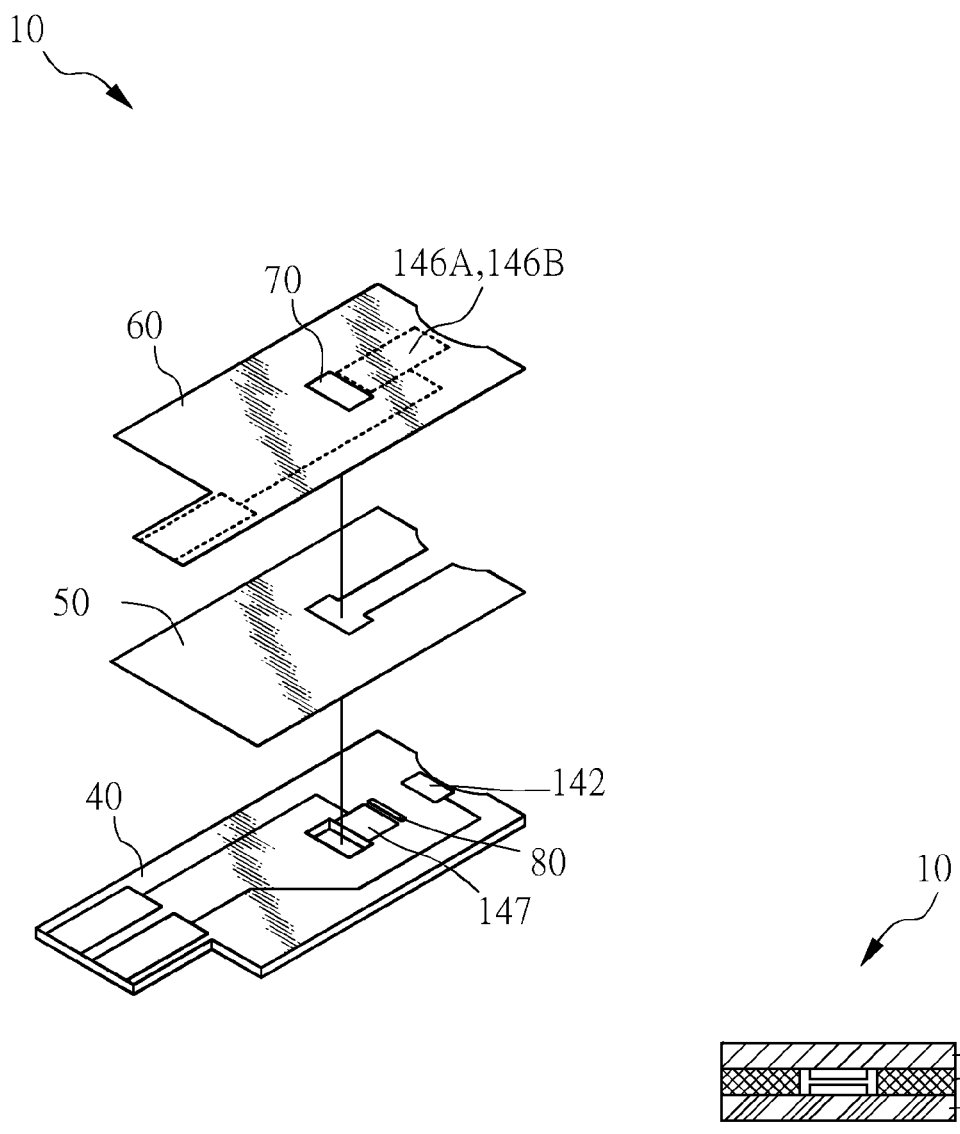
Figures 10A, 10B:
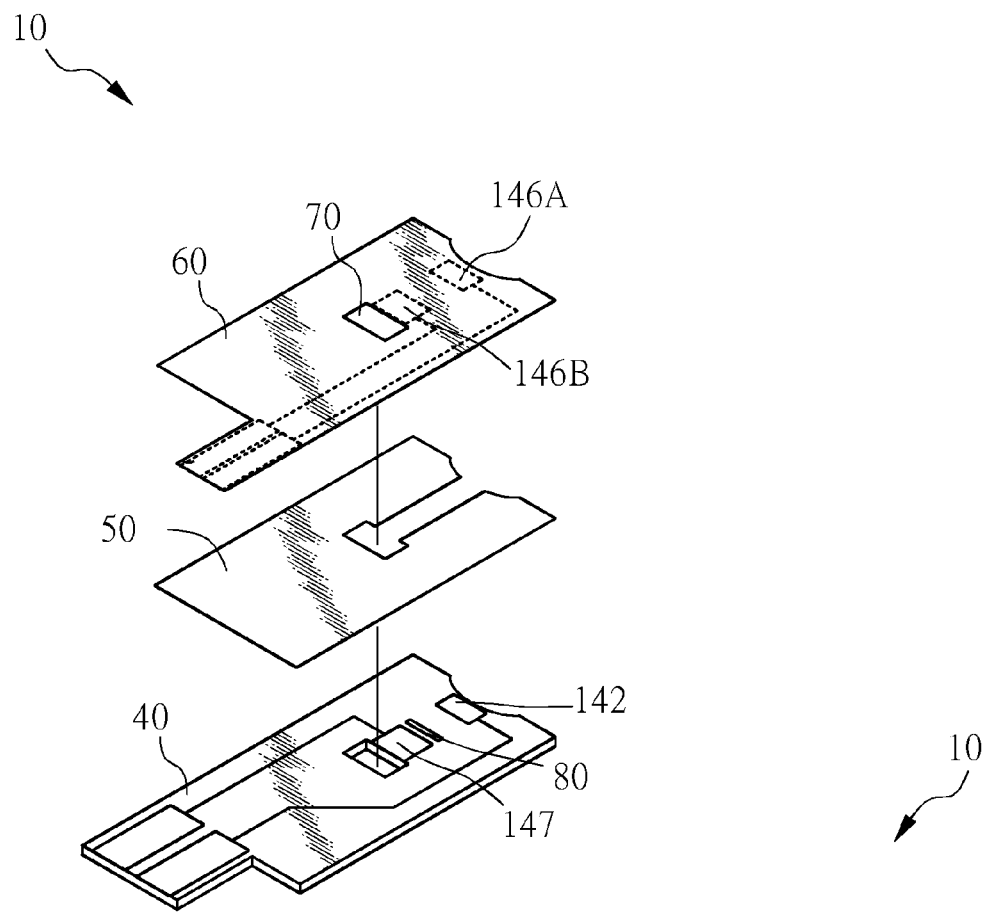
Figures 11A, 11B:
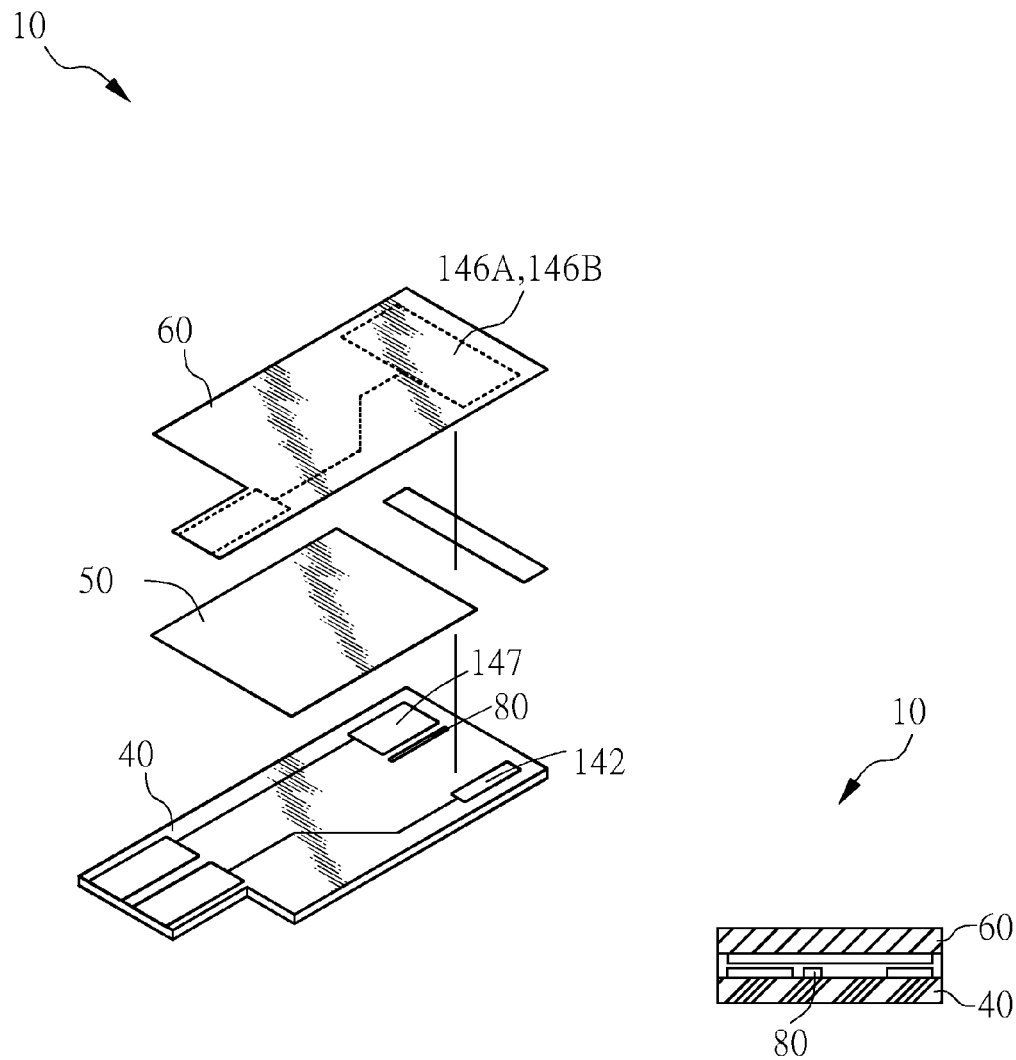

Please refer to FIG. 2 to FIG. 2B for the detecting device of the present invention. FIG. 2 illustrates a view of using the detecting device to detect according to an embodiment of the present invention; FIG. 3A to FIG. 12B illustrate various structures of the test strip of the detecting device according to an embodiment of the present invention.

First, please refer to FIG. 2, according to an embodiment of the present invention, the present invention provides a detecting device 1 comprising a test strip 10 and an electrochemical instrument 20. The test strip 10 is inserted into the electrochemical instrument 20 and works with the electrochemical instrument 20 to detect the specimen 30. In an embodiment of the present invention, the specimen 30 can be blood, urine, saliva, or the like.

In an embodiment of the present invention, the test strip 10 is connected with the electrochemical instrument 20 through a slot of the electrochemical instrument 20, so the user can just insert one end of the test strip 10 that comprises the exposed electrodes to the slot.

As shown in FIG. 2, according to an embodiment of the present invention, the present invention provides a test strip 10 comprising: a first specimen path 12A, a first electrode set 14A, a second specimen path 12B, a second electrode set 14B and a reaction reagent 16. Wherein, the second specimen path 12B is connected to the first specimen path 12A, so that the second specimen path 12B and the first specimen path 12A form a cascaded mode.

In an embodiment of the invention, the first electrode set 14A and the second electrode set 14B can be made of any conducting materials such as Pd, Au, Pt, Ag, Ir, C, Indium Tin Oxide, Indium Zinc Oxide, Cu, Al, Ga, Fe, Hg, Ta, Ti, Zr, Ni, Os, Re, Rh, Pd, organic metal and other conductive materials. Furthermore, each electrode set can be formed by sputtering, vapor deposition, screen printing or any other suitable manufacturing methods. For example, one or more electrode can be made at least partly by sputtering, deposition, supersonic vaporization, pressurized vaporization, direct writing, mask etching, or laser ablation.

As shown in FIG. 2, the first specimen path 12A comprises an inlet end 122; at least a portion of the first electrode set 14A is disposed in the first specimen path 12A; the first electrode set 14A comprises a first electrode 142 and a first reference electrode 146A. The second specimen path 12B comprises a discharge end 124; at least a portion of the second electrode set 14B is disposed in the second specimen path 12B; the second electrode set 14B comprises at least a working electrode 147 and a second reference electrode 146B. The reaction reagent 16 is disposed in the second specimen path 12B, and the reaction reagent 16 at least comprises a specific enzyme for detecting the concentration of the analyte of the specimen 30. In an embodiment of the present invention, the reaction reagent 16 also comprises polymeric binders, buffers, surfactants, and electron transfer mediators. In an embodiment of the present invention, the analyte can be blood glucose, lipid, cholesterol, uric acid, alcohol, triglycerides, ketone body, creatinine, lactic acid, haem, or the like.

It is noted that since enzymes could affect the accuracy of fluidity test, therefore, in an embodiment of the present invention, the first specimen path 12A of the present invention does not comprise any enzyme to avoid affecting the fluidity test in the first specimen path 12A. Besides, a water isolating bar (or water isolating layer) or a middle spacing bar 80 is disposed between the first specimen path 12A and the second specimen path 12B to keep the reaction reagent 16 in the second specimen path 12B from mixing with the first specimen path 12A.

As shown in FIG. 2, the test strip 10 can work with the electrochemical instrument 20 to detect the specimen 30. At least a portion of the first electrode 142 and the first reference electrode 146A are disposed in the first specimen path 12A; the first electrode 142A and the first reference electrode 146A are separated from one another. Besides, the reaction reagent 16 and a least a portion of the working electrode 147 and the second reference electrode 146B are disposed in the second specimen path 12B; wherein the working electrode 147 and the second reference electrode 146B are separated from each other.

Therefore, before the specimen 30 is detected, the first electrode 142 and the first reference electrode 146A are electrically isolated from one another, the working electrode 147 and the second reference electrode 146B are electrically isolated from each other. As shown in FIG. 2, when starting the detection for the specimen 30, the specimen 30 enters the first specimen path 12A through the inlet 122, and becomes conductivity due to the voltage applied by the electrochemical instrument 20. When the specimen 30 contacts with the first electrode 142 and the first reference electrode 146A, it generates a first impulse signal; when the specimen 30 contacts with the first reference electrode 146A and the working electrode 147, it generates a second impulse signal. The first impulse signal and the second impulse signal are used for calculating a flow time of the specimen 30. The voltage applied by the electrochemical instrument 20 includes a first voltage and a second voltage. The first voltage is applied to the first electrode 142 of the first electrode set 14A; and the second voltage is applied to the working electrode 147 of the second electrode set 14B. Since there is no reaction reagent in the first specimen path 12A, the signal generated solely by the specimen 30 may be very weak or insufficient. Since the reaction reagent 16 is disposed in the second specimen path 12B, it will generate an electrochemical reaction after applied with a reaction voltage for improving the signal of the specimen 30. Hence, normally the first voltage is greater than the second voltage. The preferred first voltage is 1 to 1.5 V, and preferred second voltage is 0.2 to 0.6 V.

Furthermore, when the specimen 30 enters the second specimen path 12B, it contacts with the working electrode 147 and generates the second impulse signal. The electrochemical instrument will shut down the second voltage. The analyte of the specimen 30 will react with the reaction reagent 16 (enzyme), and then the electrochemical instrument further provides a reaction voltage for the working electrode 147 and the second reference electrode 146B to generate a reaction signal, and then to calculate the concentration of the analyte of the specimen 30 according the reaction signal. The preferred second voltage is the same as the reaction voltage.

With the first specimen path 12A cascaded with the second specimen path 12B, the flow time can be detected as the specimen 30 flows through the first specimen path 12A. There is no need to wait the specimen 30 completely flows through the second specimen path 12B. When the specimen 30 is flowing, it contacts only just a little reaction reagent 16 existed in the second specimen path 12B; therefore, the fluidity of the specimen 30 is not affected. Since there is no reaction reagent disposed in the first specimen path 12A, the issue of increasing the background value of the current can be avoided. In order to avoid that the electrode cannot be detected, the present invention increases the voltage for helping obtaining the signal. Besides, interfacial agents can be included for helping the specimen 30 to flow. In an embodiment of the present invention, the voltage applied is 1.24 V, but the present invention is not limited to that.

As shown in FIG. 2, taking account of air pressure and in order to let the specimen 30 flow in the first specimen path 12A and the second specimen path 12B without being blocked by air, test strip 10 comprises the discharge end 124. When the specimen 30 is drawn into the first specimen path 12A and the second specimen path 12B, air existed in front of the specimen 30 can be discharged to facilitate flowing of the specimen 30. By the design of the discharge end 124, when the specimen 30 enters the first specimen path 12A and the second specimen path 12B, it will move towards the discharge end 124. When flowing in the first specimen path 12A, the specimen 30 will be in contact with the first electrode 142, and then in contact within the first reference electrode 146A. Therefore, when the specimen 30 enters the first specimen path 12A, it becomes conductivity due to the voltage applied by the electrochemical instrument 20. As the specimen 30 flows along the first specimen path 12A to makes contact with the first electrode 142 and the first reference electrode 146A, it forms a conducting loop with the first electrode 142 and the first reference electrode 146A to generate a first impulse signal. Consequently, as the specimen 30 flows along the second specimen path 12B to make contact with the working electrode 147, it forms another conducting loop with the first reference electrode 146A and the working electrode 147 to generate the second impulse signal.

Thereafter, the electrochemical instrument 20 can calculate a flow time of the specimen 30 according to the first impulse signal and the second impulse signal and then obtain a viscosity of the specimen 30 based on the flow time. Since the distances between the first electrode 142, the first reference electrode 146A and the working electrode 147 are predetermined, the flow rate can be obtained by using the distances and a time difference between the first impulse signal and the second impulse signal, and the viscosity of the specimen 30 can be obtained as well. Since the calculation of the viscosity based on the flow time is known in the art, it will not be further described.

As shown in FIG. 2, the specimen 30 flows both in the first specimen path 12A and the second specimen path 12B. When the specimen 30 flows in the second specimen path 12B, it will first make contact with a specific enzyme in the reaction reagent 16 and react with the analyte of the specimen 30; then the specimen 30 will be in contact with the second reference electrode 146B and the working electrode 147 sequentially to obtain a concentration of the analyte of the specimen 30.

As shown in FIG. 2, the present invention does not dispose the reaction reagent in the first specimen path 12A, but disposes the reaction reagent 16 in the second specimen path 12B to obtain the flow time and the analyte concentration of the specimen 30. Since there is no reagent disposed in the first specimen path 12A but there is a reagent disposed the second specimen path 12B respectively for doing different detecting jobs, so it is possible to detect the flow time and the analyte concentration separated without interference. Besides, since there is no reagent in the first specimen path 12A, the fluidity of the specimen 30 will not be affected, thereby improving the detection of the flow time of the specimen 30 and obtaining the precise viscosity of the specimen 30. The present invention can also use the accurate flow time to correct the concentration of the analyte of the specimen 30 and to obtain an accurate concentration of the analyte.

The present invention does not use reaction reagent but increase the voltage to detect the flow time of the specimen 30 with fast and immediate effects; therefore, the flow time of the specimen 30 can be obtained before knowing the concentration of the analyte of the specimen 30.

In an embodiment of the present invention, the specimen 30 is blood, and the concentration of the analyte refers to the concentration of blood glucose. Since blood is a mixture of many physiological substances, when using an electrochemical method to obtain the concentration of an analyte of blood, it is necessary to go through corrections and compensation steps to obtain an accurate result. For example, the concentration of blood glucose varies with different hematocrits. While the normal value of hematocrit is between 35 to 55%, the hematocrit value for anemia patients would be lower, and the hematocrit value for babies would be little higher, making it difficult to judge whether the hematocrit value is within a normal range. Besides, US standards for clinical diagnosis center listed sixteen electrochemical interference substances, which include: paracetamol, Vitamin C, salicylic acid, tolbutamide, tetracycline, tolinase, dopamine, bilirubin, ephedrine, cholesterol, Ibuprofen, creatinine, L-dopa, triglycerides, methyldopa, urate.

In the prior art technique, in order to measure the concentration of the analyte in the presence of red blood cells as an interference substance, U.S. Pat. No. 7,407,811 discloses a method of measuring an analyte in a biological fluid comprises applying an excitation signal having a DC component and an AC component. The AC responses comprising a phase angle and an admittance value are measured; a corrected DC response is determined using the AC response; and a concentration of the analyte is determined based upon the corrected DC response, thereby obtaining the hematocrit. In addition, US patent application No. 2011/0139634 A1 also discloses a method of detecting hematocrit by applying AC signals with constant frequency. In an embodiment of the present invention, after the electrochemical instrument 20 obtains the flow time of the specimen 30, the electrochemical instrument 20 can provide an AC signal to the first electrode set 14A to let the specimen 30 generate a reaction current, which is used for calculating a hematocrit. Afterwards, the hematocrit obtained from the reaction current and the hematocrit obtained from the flow time are compared, if the two values are close, then the concentration of the analyte is corrected and calculated by the flow time to obtain a more accurate concentration of the analyte; if a difference between the two values exceeds a predetermined range, then an error alert is issued to a user. The technique of using AC signals to compensate the concentration of the analyte has been disclosed in U.S. Pat. No. 7,407,811 and US patent application No. 2011/0139634 A1, which are both incorporated by reference in the present invention.

There are more than one analytes in a blood sample, other substances such as urea, acetaminophen, vitamin C, dihydroxy benzoic acid also exist, and these substances can be oxidizers or reducers. When an electrochemical reaction occurs, these substances would all participate in the electrochemical reaction; therefore, the electrochemical instrument 20 needs to correct or compensate the response signal obtained. In an embodiment of the present invention, after the electrochemical instrument 20 of the present invention obtains the flow time of the specimen 30, the electrochemical instrument 20 provides a voltage to the first electrode set 14A to let the specimen 30 generate a electrochemical reaction current; this electrochemical reaction current should be the background current of the blood sample or come from interference substances, it is not the reaction current of the concentration of the analyte. Therefore, this electrochemical reaction current could be used to calculate and correct the concentration of the analyte, thereby obtaining a more accurate analyte concentration. In the present invention the voltage used to detect the background current has the same voltage level as that used to detect the concentration of the analyte. Besides, when this electrochemical reaction current is used to compensate the concentration of the analyte, a positive or negative compensation could be achieved. U.S. Pat. No. 7,653,492 discloses a method of reducing the effect of interference in a specimen when measuring an analyte using an electrochemical sensor. This patent document is incorporated by reference in the present invention and will not be further described.

As shown in FIG. 2, in an embodiment of the present invention, the first electrode 142 in the first specimen path 12A is disposed near the inlet end 122 of the first specimen path 12A, and the first reference electrode 146A is disposed between the first electrode 142 and the working electrode 147; however, the first electrode set 14A and the second electrode set 14B can be configured differently, which will be described later.

As shown in FIG. 2, in an embodiment of the present invention, the reaction reagent 16 covers at least a portion of the second electrode set 14B in the second specimen path 12B; however, in an embodiment of the present invention, the reaction reagent 16 can be configured differently as long as the specimen 30 can react with the enzymes when the specimen 30 is in contact with the second electrode set 14B. Different configurations of the reaction reagent 16 will be described later.

As shown in FIG. 2, in an embodiment of the present invention, the inlet end 122 of the first specimen path 12A is disposed at a front end of the test strip 10. Alternatively, the inlet end 122 of the first specimen path 12 can be disposed at a side of the test strip 10; other configurations are also possible and will be descried later.

As shown in FIG. 2, in an embodiment of the present invention, the first electrode set 14A comprises the first electrode 142 and the first reference electrode 146A; however, the first electrode set 14A can also comprise other additional electrodes to improve the accuracy in calculating the flow time. Furthermore, as shown in FIG. 2, in an embodiment of the present invention, the second electrode set 14B comprises the working electrode 147 and the second reference electrode 146B; however, the second electrode set 14B of the present invention can comprise other additional electrodes to improve the accuracy in calculating the concentration of the analyte, which will be described later.

Figure 12A:
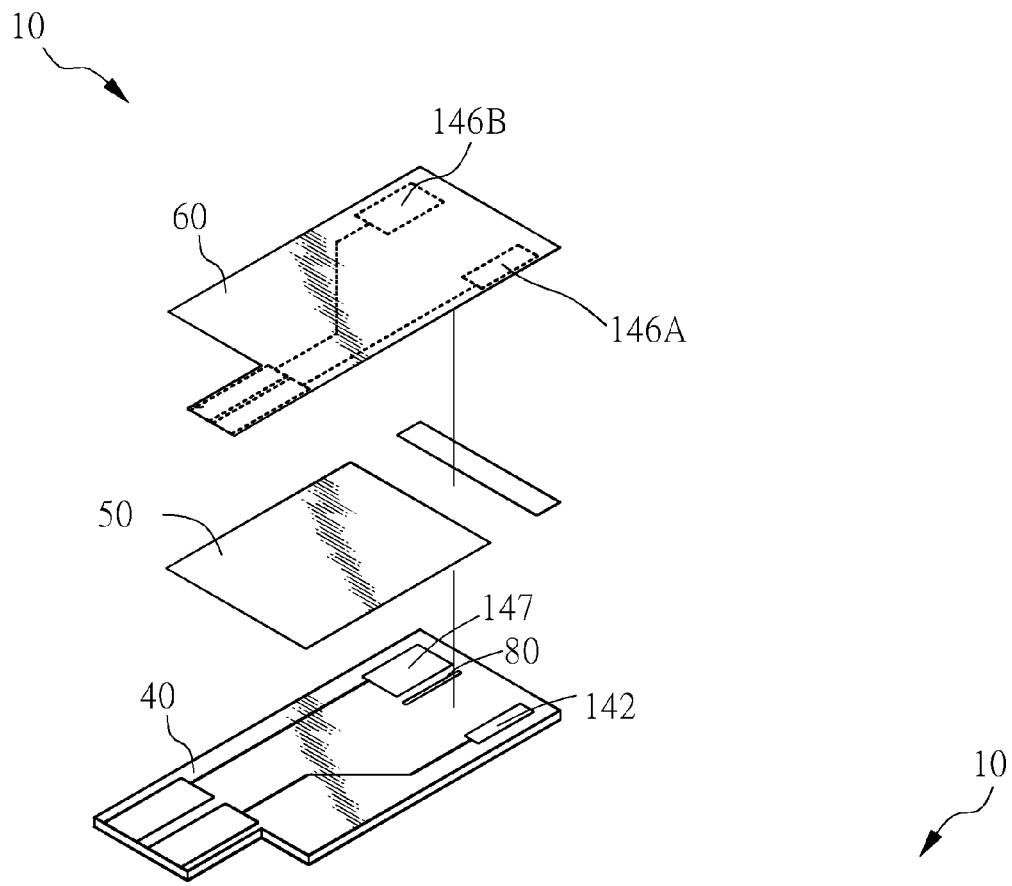
Figure 12B:
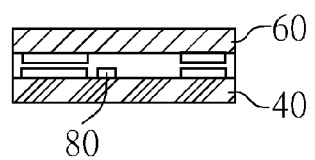

Please refer to FIG. 3A to FIG. 12B for various structures of the test strip of the detecting device according to an embodiment of the present invention. As shown in FIG. 3A, FIG. 4A, FIG. 5A and FIG. 6A, the test strip 10 comprises the substrate 40, the spacer layer 50, and the cap layer 60; FIG. 3B to FIG. 3I illustrate various embodiments of the substrate 40 shown in FIG. 3A; FIG. 5B to FIG. 5I illustrate various embodiments of the substrate 40 shown in FIG. 5A; FIG. 6B to FIG. 6I illustrate various embodiments of the substrate 40 shown in FIG. 6A. As shown in FIG. 7A, FIG. 7C, FIG. 8A, and FIG. 8C, the test strip 10 comprises the substrate 40, the gasket layer 90, the spacer layer 50, and the cap layer 60; FIG. 7B illustrates a variation of the substrate 40 shown in FIG. 7A; FIG. 7D illustrates a variation of the substrate 40 shown in FIG. 7C; FIG. 8B illustrates a variation of the substrate 40 shown in FIG. 8A; and FIG. 8D illustrates a variation of the substrate 40 shown in FIG. 8C. As shown in FIG. 9A, FIG. 10A, FIG. 11A, and FIG. 12A, the test strip 10 comprises the substrate 40, the spacer layer 50, and the cap layer 60; FIG. 9B illustrates test strip 10 of FIG. 9A in a combined state; FIG. 10B illustrates test strip 10 of FIG. 10A in a combined state; FIG. 11B illustrates test strip 10 of FIG. 11A in a combined state; and FIG. 12B illustrates test strip 10 of FIG. 12A in a combined state.

As shown in FIG. 3A, in an embodiment of the present invention, the test strip 10 of the present invention comprises a substrate 40, a spacer layer 50 and a cover layer 60. In the embodiment, the first electrode set 14A and the second electrode set 14B are disposed on the substrate 40; the spacer layer 50 covers the substrate 40 and exposes a portion of the first electrode set 14A and the second electrode set 14B; and the cover layer 60 covers the spacer layer 50, thereby forming the first specimen path 12A and the second specimen path 12B.

As shown in FIG. 3A to FIG. 3G, FIG. 4A to FIG. 4G, FIG. 5A to FIG. 5G, FIG. 6A to FIG. 6G, and FIG. 7A to FIG. 12B, the test strip 10 comprises only one time detecting electrode (i.e., the first electrode 142) and treats the working electrode 147 as the second time detecting electrode; therefore, the present invention can use one less electrode and still can have the first impulse signal and the second impulse signal generated. Besides, when using the test strip 10 to detect the flow time, the specimen 30 would be in contact with only a little amount of enzymes, thereby reducing the effect of the enzymes.

In an embodiment of the present invention shown in FIG. 3A to FIG. 12B, in order to avoid the two reagents mixing with each other, a middle spacing bar (isolating bar) 80 can be disposed between the first specimen path 12A and the second specimen path 12B (as shown in FIG. 3A to FIG. 3C, FIG. 3H to FIG. 3I, FIG. 4A to FIG. 4C, FIG. 4H to FIG. 4I, FIG. 5B to FIG. 5D, FIG. 5H to FIG. 5I, FIG. 6B to FIG. 6D, FIG. 9A to FIG. 12B); however, there can be other configurations for the present invention. In an embodiment of the present invention, the middle spacing bar 80 can be disposed on the first reference electrode 146A (as shown in FIG. 3D, FIG. 4D, FIG. 5E, FIG. 6E); besides, in order to keep the reaction reagent 16 away from affecting the flow time detection, the working electrode 147 can be extended into the first specimen path 12A (as shown in FIG. 3E to FIG. 3G, FIG. 4E to FIG. 4G, FIG. 5A, FIG. 5F, FIG. 5G, FIG. 6A, FIG. 6F, FIG. 6G, FIG. 7A to FIG. 7D, FIG. 8A to FIG. 8D). In an embodiment of the present invention, the working electrode 147 can be formed in a bar or a fork shape, and the middle spacing bar 80 is disposed on the working electrode 147 or between the forks of the working electrode 147. With regards to the embodiment that the working electrode 147 is extended to the first specimen path, since the working electrode 147 disposed in the first specimen path 12A does not cover the reaction reagent 16, the electrochemical instrument 20 needs to provide higher voltage to produce sufficient reaction signal. Therefore, in this embodiment, the first voltage and the second voltage provided by the electrochemical instrument 20 should be the same.

In an embodiment of the present invention, the second electrode set 14B of the detecting device 1 further comprises a detector electrode 149 (as shown in FIG. 3B, FIG. 4B, FIG. 5C, FIG. 6C) disposed near the discharge end 124 of the second specimen path 12B. The detector electrode 149 is provided for determining whether the second specimen path 12B is filled up with the specimen 30 to make sure that the second specimen path 12B has been filled up with the specimen 30 before detecting the concentration of the analyte.

In an embodiment of the present invention, the first electrode set 14A of the test strip 10 further comprises a second electrode 144. When the specimen 30 flows through the second electrode 144 and the first reference electrode 146A, a third impulse signal is generated, wherein the third impulse signal is used with the first impulse signal and the second impulse signal to obtain the flow time of the specimen 30, thereby obtaining the viscosity of the of the specimen 30. As shown in FIG. 3I, FIG. 4I, FIG. 5H and FIG. 6H, the second electrode 144 is disposed between the first electrode 142 and the working electrode 147; however, the present invention can have other configurations. As shown in FIG. 3H, FIG. 4H, FIG. 5I and FIG. 6I, the second electrode 144 can be disposed near the first electrode 142. By using the second electrode 144, at least two sets of flow time values are obtained; if the two sets of flow time values are very different from each other, then an error alert is issued to a user.

In an embodiment of the present invention, when the first specimen path 12A is cascaded with the second specimen path 12B in the test strip 10, the inlet end 122 of the first specimen path 12A can be disposed at a front end (as shown in FIG. 3A to FIG. 3I, FIG. 4A to FIG. 4I, FIG. 8A to FIG. 8D, FIG. 9A to FIG. 9B and FIG. 10A to FIG. 10B) or a side (as shown in FIG. 5A to FIG. 5I, FIG. 6A to FIG. 6I, FIG. 7A to FIG. 7D, FIG. 11A to FIG. 11B and FIG. 12A to FIG. 12B) of the test strip 10.

In an embodiment of the present invention, the test strip 10 comprise a through hole 70 communicating with the discharge end 124 of the second specimen path 12B (as shown in FIG. 3A, FIG. 4A, FIG. 8A, FIG. 8C, FIG. 9A to FIG. 9B, and FIG. 10A to FIG. 10B) to increase the area for discharging air for the specimen 30. The through hole is disposed to stop the specimen 30 at the discharge end, so the specimen 30 will flow in the capillary and will not be dragged by the cap layer 60 or the substrate 40 to leave the capillary. It is noted that the present invention can have discharge holes disposed on the cap layer 60 or the substrate 40 respectively without using the through hole 70 and can still serve the purpose.

In an embodiment of the present invention, the first specimen path 12A and the second specimen path 12B can have the same width (as shown in FIG. 3A, FIG. 5A, FIG. 7A, FIG. 8A, and FIG. 9A to FIG. 12B); or the first specimen path 12A has a width smaller than that of the second specimen path 12B (as shown in FIG. 4A, FIG. 6A, FIG. 7C, and FIG. 8C).

In an embodiment of the present invention, the first reference electrode 146A and the second reference electrode 146B of the test strip 10 can be disposed on the lower surface of the cover layer 60 (shown in FIG. 9A to FIG. 12B) to form a stack configuration, wherein the first reference electrode 146A and the second reference electrode 146B can be the same electrode (as shown in FIG. 9A, FIG. 9B, FIG. 11A, and FIG. 11B).

As shown in FIG. 7A to FIG. 7D and FIG. 8A to FIG. 8D, in an embodiment of the present invention, the test strip 10 can also comprise a gasket layer 90 disposed between the substrate 40 and the spacer layer 50 to separate the first specimen path 12A and the second specimen path 12B. The gasket layer 90 can be formed by screen printing an insulating layer or by attaching a spacer layer.

Finally, the present invention provides a detecting method working with an electrochemical instrument to detect a specimen. In the following, the detecting device 1 and the test strip 10 are used to understand the detecting method of the present invention; however, the detecting method of the present invention can also use devices other than the detecting device and the test strip 10.

Figure 13:
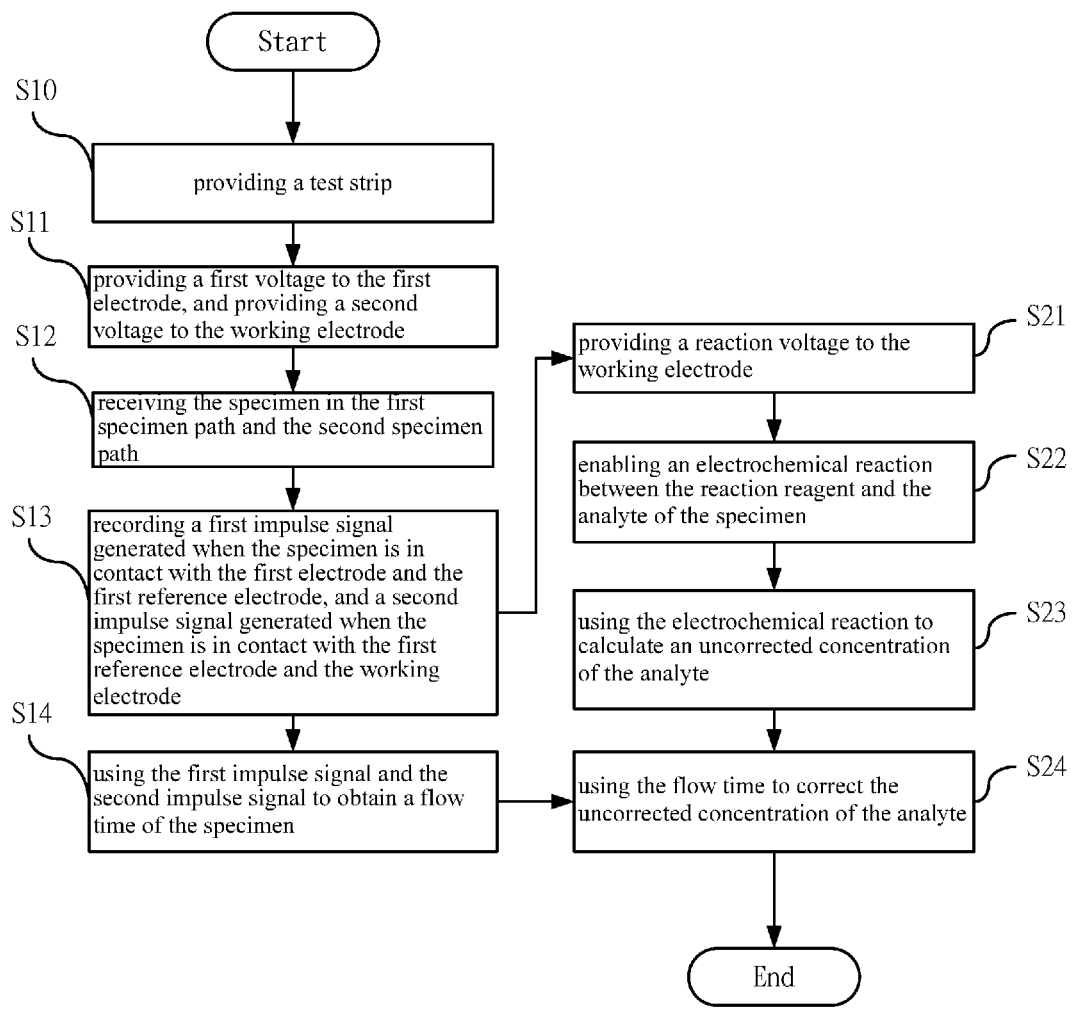
FIG. 13 to FIG. 16 illustrate flow charts of a detecting method according to an embodiment of the present invention.

As shown in FIG. 13, the present invention first proceeds to step S10: providing a test strip according to an embodiment of the present invention. Then the method proceeds to step S11: providing a first voltage to the first electrode, and providing a second voltage to the working electrode; step S12: receiving the specimen in the first specimen path and the second specimen path; step S13: recording a first impulse signal generated when the specimen is in contact with the first electrode and the first reference electrode, and a second impulse signal generated when the specimen is in contact with the first reference electrode and the working electrode; and step S14: using the first impulse signal and the second impulse signal to obtain a flow time of the specimen.

As shown in FIG. 13, after step S13, the detecting method of the present invention proceeds step S21 to S23, which can be alternatively proceeded after the detector electrode detecting that the second specimen path is filled with the specimen. As shown in FIG. 13, the method proceeds to step S21: providing a reaction voltage to the working electrode; step S22: enabling an electrochemical reaction between the reaction reagent and the analyte of the specimen; step S23: using the electrochemical reaction to calculate an uncorrected concentration of the analyte; and step S24: using the flow time to correct the uncorrected concentration of the analyte.

Figure 14:
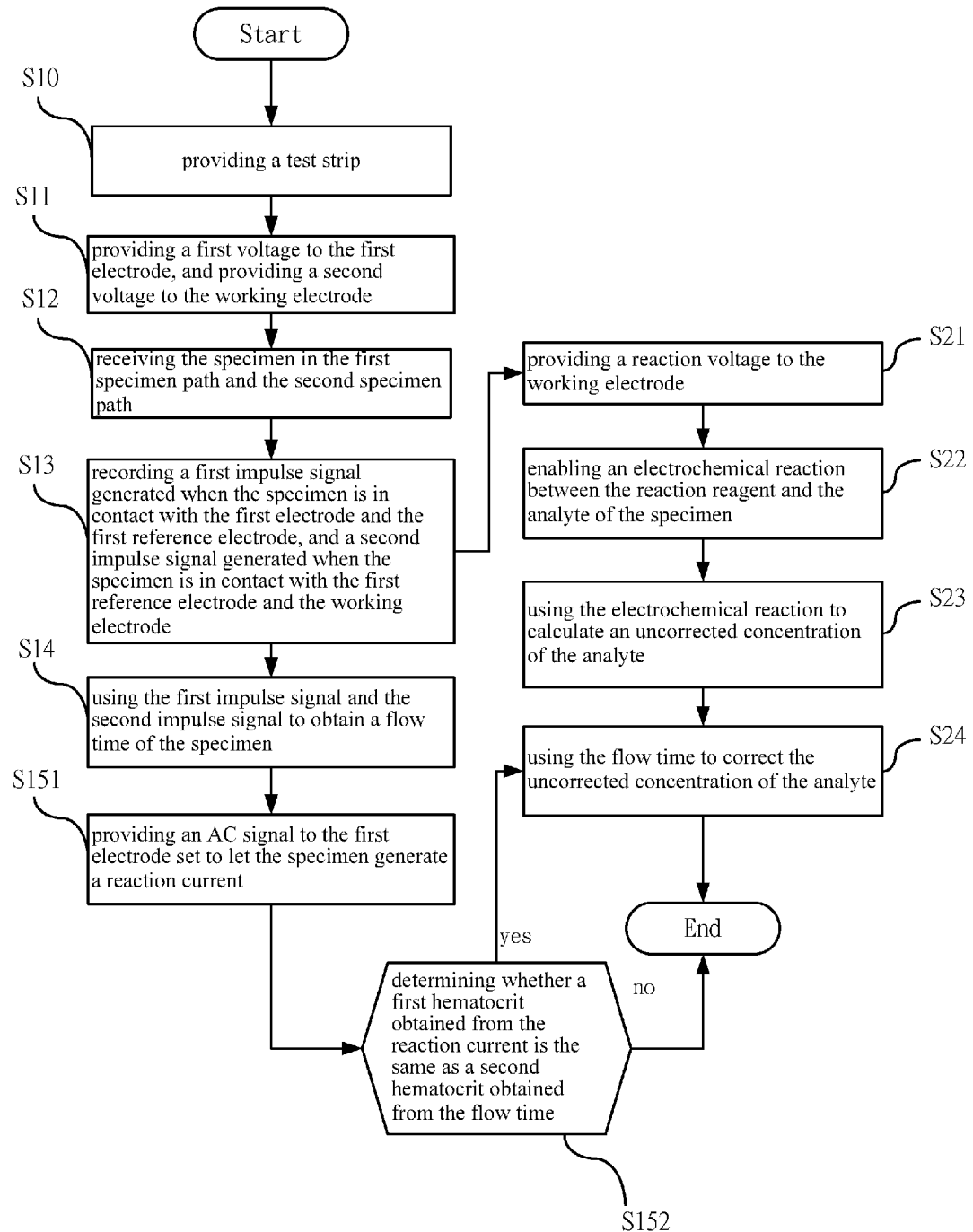

Furthermore, as shown in FIG. 14, in order to obtain a more accurate concentration of the analyte, after step S14, the detecting method of the present invention proceeds to step S151: providing an AC signal to the first electrode set to let the specimen generate a reaction current; step S152: determining whether a first hematocrit obtained from the reaction current is the same as a second hematocrit obtained from the flow time. If the first hematocrit is very different from the second hematocrit, then the specimen does not flow normally, the detection is invalid, and the detecting method is terminated; if the first hematocrit is close to the second hematocrit, then the specimen flows normally, the detection is valid, and the method proceeds to step S24: using the flow time to correct the uncorrected concentration of the analyte. Since using the AC signal to compensate the concentration of the analyte is well known in the art, it will not be further described for the sake of brevity.

Figure 15:
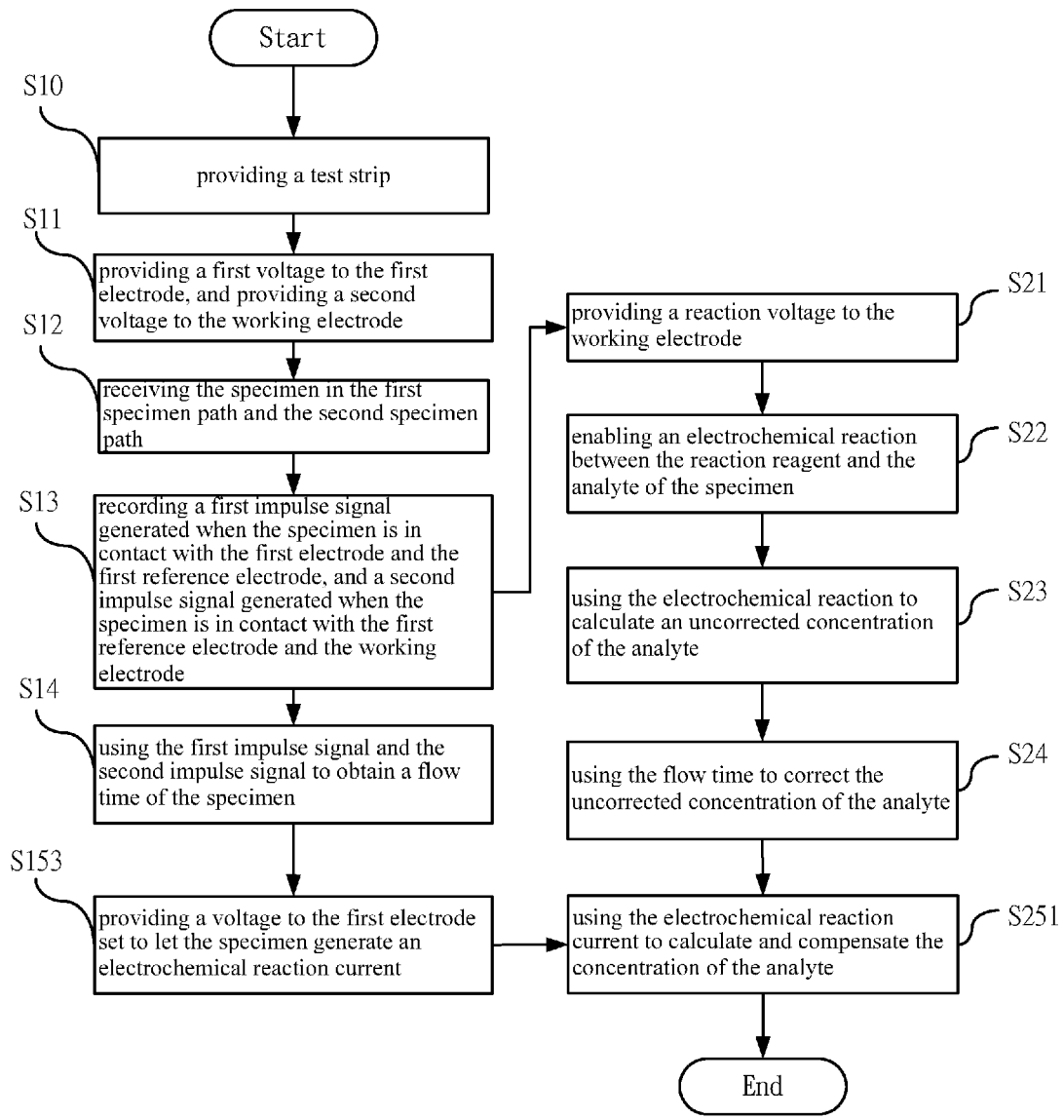

Furthermore, as shown in FIG. 15, in order to obtain a more accurate concentration of the analyte, after step S14, the detecting method of the present invention proceeds to step S153: providing a voltage to the first electrode set to let the specimen generate an electrochemical reaction current. Thereafter, in addition to step S24: using the flow time to correct the uncorrected concentration of the analyte, the method further proceeds to step S251: using the electrochemical reaction current to calculate and compensate the concentration of the analyte. Since the step of using the electrochemical reaction current to calculate and compensate the concentration of the analyte is well known in the art, it will not be further described for the sake of brevity.

Figure 16:
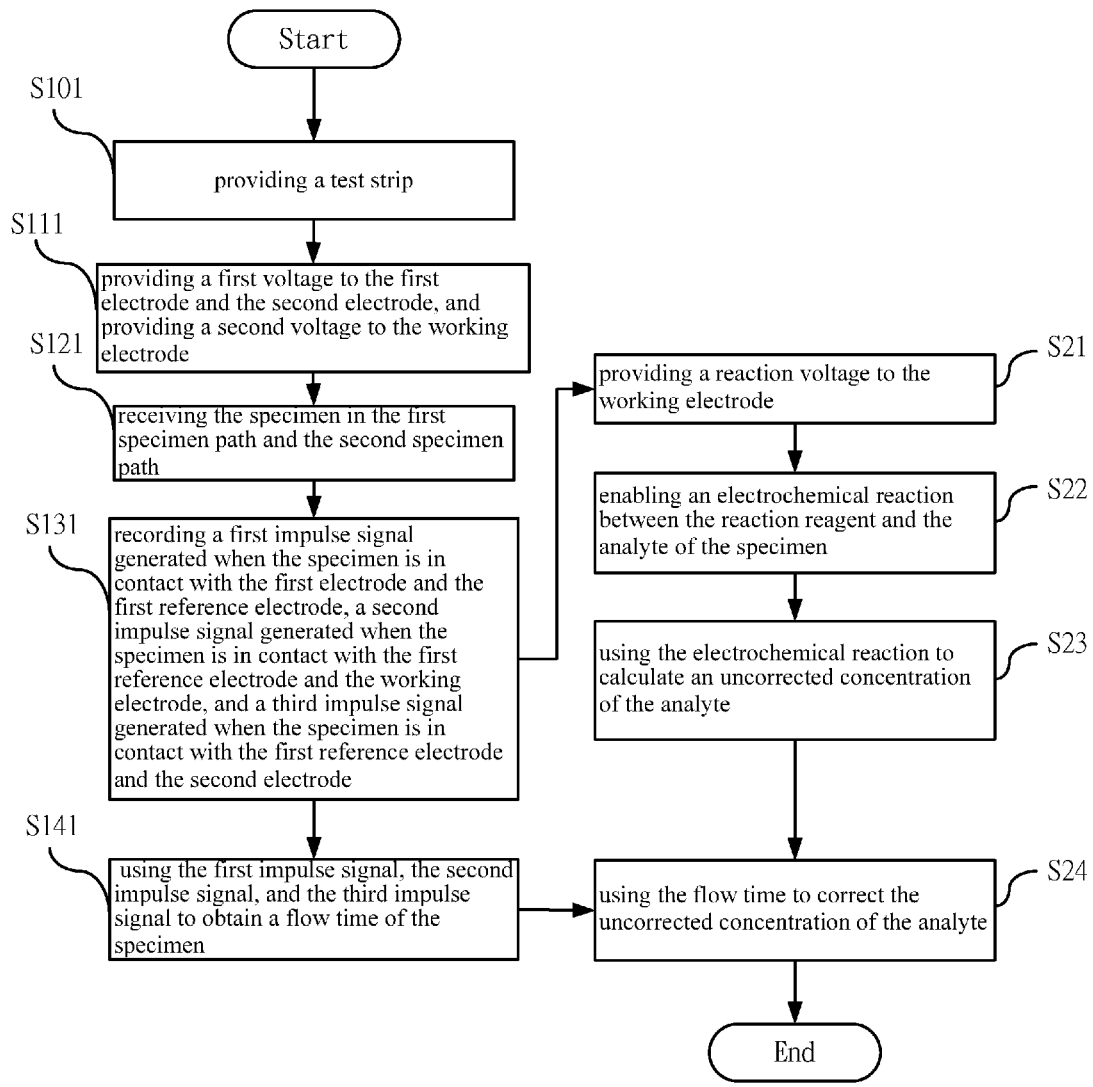

As shown in FIG. 3H, FIG. 3I, FIG. 4H, FIG. 4I, FIG. 5H, FIG. 5I, FIG. 6H and FIG. 6I, in an embodiment of the present invention, the detecting method of the present invention provides a plurality of electrode for detecting time for accurately detecting the flow time. As show in FIG. 16, in an embodiment of the present invention, the detecting method of the present invention includes step S101: providing a test strip according to an embodiment of the present invention; step S111 providing a first voltage to the first electrode and the second electrode, and providing a second voltage to the working electrode; step S121: receiving the specimen in the first specimen path and the second specimen path; step S131: recording a first impulse signal generated when the specimen is in contact with the first electrode and the first reference electrode, a second impulse signal generated when the specimen is in contact with the first reference electrode and the working electrode, and a third impulse signal generated when the specimen is in contact with the first reference electrode and the second electrode; step S141: using the first impulse signal, the second impulse signal, and the third impulse signal to obtain a flow time of the specimen; and step S24: using the flow time to correct the uncorrected concentration of the analyte.

It is noted that the above-mentioned embodiments are only for illustration. It is intended that the present invention cover modifications and variations of this invention provided they fall within the scope of the following claims and their equivalents. Therefore, it will be apparent to those skilled in the art that various modifications and variations can be made to the structure of the present invention without departing from the scope or spirit of the invention.

REFERENCE NUMERALS

| [Reference Numerals] | |
|---|---|
| detecting device 1 | test strip 10 |
| first specimen path 12A | second specimen path 12B |
| inlet end 122 | discharge end 124 |
| first electrode set 14A | second electrode set 14B |
| first electrode 142 | second electrode 144 |
| first reference electrode 146A | second reference electrode 146B |
| working electrode 147 | detector electrode 149 |
| reaction reagent 16 | electrochemical instrument 20 |
| specimen 30 | substrate 40 |
| spacer layer 50 | cap layer 60 |
| through hole 70 | middle spacing bar 80 |
| gasket layer 90 | |

What is claimed is:

1. A test strip used with an electrochemical instrument to detect a specimen, the test strip comprising:
a first specimen path comprising an inlet end;
a first electrode set having at least a portion thereof disposed in the first specimen path, the first electrode set at least comprising a first electrode and a first reference electrode;
a second specimen path comprising a discharge end, the second specimen path connected to the first specimen path, wherein the first specimen path and the second specimen path are aligned and adjacent, such that the inlet end is the inlet end for the first specimen path and the second specimen path;
an isolating bar or a middle spacing bar disposed between the first specimen path and the second specimen path;
a second electrode set having at least a portion thereof disposed in the second specimen path, the second electrode set at least comprising a working electrode and a second reference electrode, the working electrode extending into the first specimen path, the working electrode being formed in a bar shape or a fork shape, the working electrode having the isolating bar or the middle spacing bar disposed thereon or therebetween;
a reaction reagent disposed in the second specimen path, and there is no reagent disposed in the first specimen path, the reaction reagent at least comprising an enzyme for detecting a concentration of an analyte of the specimen;
when the test strip receives a first voltage and a second voltage, a first impulse signal is generated when the specimen is in contact with the first electrode and the first reference electrode, and a second impulse signal is generated when the specimen is in contact with the first reference electrode and the working electrode, thereby obtaining a flow time of the specimen according to the first impulse signal and the second impulse signal, and the flow time can be used to correct the concentration of the analyte of the specimen.

2. The test strip as claimed in claim 1, wherein the first voltage is substantially 1.24 V.

3. The test strip as claimed in claim 1, wherein the second electrode set further comprises a detector electrode disposed near the discharge end of the second specimen path.

4. The test strip as claimed in claim 1, wherein the first reference electrode and the second reference electrode are the same electrode.

5. The test strip as claimed in claim 1, wherein the specimen comprises blood, urine, or saliva.

6. The test strip as claimed in claim 1, wherein the analyte comprises blood glucose, lipid, cholesterol, uric acid, alcohol, triglycerides, ketone body, creatinine, lactic acid, or haem.

7. The test strip as claimed in claim 1, wherein the specimen is a blood specimen, and the concentration of the analyte is a concentration of blood glucose.

8. The test strip as claimed in claim 1, wherein the inlet end of the first specimen path is disposed at a front end or a side of the test strip.

9. The test strip as claimed in claim 1, wherein the first electrode is disposed near the inlet end of the first specimen path.

10. The test strip as claimed in claim 1, wherein the reaction reagent covers at least a portion of the second electrode set.

11. The test strip as claimed in claim 1, wherein further comprises a through hole communicating with the discharge end of the second specimen path.

12. The test strip as claimed in claim 1, wherein the first specimen path has a width less than a width of the second specimen path.

13. The test strip as claimed in claim 1, wherein the first voltage and the second voltage are the same.

14. The test strip as claimed in claim 1, wherein further comprises:
a substrate for disposing the first electrode set and the second electrode set thereon;
a spacer layer covering the substrate and exposing a portion of the first electrode set and the second electrode set; and
a cap layer covering the spacer layer to form the first specimen path and the second specimen path.

15. The test strip as claimed in claim 1, wherein further comprises:
a substrate for disposing the first electrode of the first electrode set and the working electrode of the second electrode set thereon;

a spacer layer covering the substrate, the spacer layer exposing a portion of the first electrode of the first electrode set and the working electrode of the second electrode set; and a cap layer covering the spacer layer to form the first specimen path and the second specimen path, wherein the first reference electrode of the first electrode set and the second reference electrode of the second electrode set cover a lower surface of the cap layer.

16. The test strip as claimed in claim 14, further comprising a gasket layer disposed between the substrate and the spacer layer.

17. The test strip as claimed in claim 15, further comprising a gasket layer disposed between the substrate and the spacer layer.

18. The test strip as claimed in claim 1, wherein the first electrode set at least comprises a second electrode, and a third impulse signal is generated when the specimen is in contact with the second electrode and the first reference electrode, thereby obtaining a flow time of the specimen according to the first impulse signal, the second impulse signal, and the third impulse signal.

19. The test strip as claimed in claim 18, wherein the second electrode is disposed near the first electrode.

20. The test strip as claimed in claim 18, wherein the second electrode is disposed between the first electrode and the working electrode.

21. A detecting method using an electrochemical instrument to detect a specimen, the detecting method comprising the following steps:
providing the test strip as claimed in claim 1;
providing a first voltage to the first electrode, and providing a second voltage to the working electrode;
receiving the specimen in the first specimen path and the second specimen path;
recording a first impulse signal generated when the specimen is in contact with the first electrode and the first reference electrode, and recording a second impulse signal generated when the specimen is in contact with the first reference electrode and the working electrode;
using the first impulse signal and the second impulse signal to obtain a flow time of the specimen;
providing a reaction voltage to the working electrode;
enabling an electrochemical reaction between the reaction reagent and the analyte of the specimen;
using the electrochemical reaction to calculate an uncorrected concentration of the analyte; and
using the flow time to correct the uncorrected concentration of the analyte.

22. The detecting method as claimed in claim 21, wherein further comprises:
obtaining a viscosity of the specimen according to the flow time.

23. The detecting method as claimed in claim 21, after the step of using the first impulse signal and the second impulse signal to obtain a flow time of the specimen, the detecting method comprising:
providing an AC signal to the first electrode set to let the specimen generate a reaction current; and
determining whether a first hematocrit obtained from the reaction current is the same as a second hematocrit obtained from the flow time.

24. The detecting method as claimed in claim 21, after the step of using the first impulse signal and the second impulse signal to obtain a flow time of the specimen, the detecting method comprising:
providing a voltage to the first electrode set to let the specimen generate an electrochemical reaction current; and
using the electrochemical reaction current to calculate and compensate the concentration of the analyte.

25. A detecting method using an electrochemical instrument to detect a specimen, the detecting method comprising the following steps:
providing the test strip as claimed in claim 18;
providing a first voltage to the first electrode and the second electrode, and providing a second voltage to the working electrode;
receiving the specimen in the first specimen path and the second specimen path;
recording a first impulse signal generated when the specimen is in contact with the first electrode and the first reference electrode, a second impulse signal generated when the specimen is in contact with the first reference electrode and the working electrode, and a third impulse signal generated when the specimen is in contact with the first reference electrode and the second electrode;
using the first impulse signal, the second impulse signal and the third impulse signal to obtain a flow time of the specimen;
providing a reaction voltage to the working electrode;
enabling an electrochemical reaction between the reaction reagent and the analyte of the specimen;
using the electrochemical reaction to calculate an uncorrected concentration of the analyte; and
using the flow time to correct the uncorrected concentration of the analyte.

* * * * *